United States Patent [19]

Fischer et al.

[11] 4,248,972

[45] Feb. 3, 1981

[54] STACKED MODULES FOR ANAEROBIC DIGESTION

[75] Inventors: David J. Fischer; Richard M. Narske, both of Sarasota; John C. Thomas, Orlando; Edward J. Worthington, Jr., Sarasota, all of Fla.

[73] Assignee: Universal Research and Development Corp., Tallevast, Fla.

[21] Appl. No.: 92,578

[22] Filed: Nov. 8, 1979

[51] Int. Cl.³ .............................................. C12M 1/02
[52] U.S. Cl. ...................... 435/292; 48/111; 422/193; 422/201; 435/316; 435/801; 435/819; 210/180
[58] Field of Search ........... 71/10, 12; 78/111, 197 A; 210/1, 2, 10, 16, 17, 71, 73 S, 180, 189, 12; 422/184, 187, 193, 201; 435/290, 316, 801, 819, 292

[56] References Cited

U.S. PATENT DOCUMENTS

| | | | |
|---|---|---|---|
| 1,806,698 | 5/1931 | Miller | 435/316 |
| 2,043,265 | 6/1936 | Roeder | 210/10 |
| 2,222,651 | 11/1940 | Breuchaud | 435/801 |
| 3,156,646 | 11/1964 | Cameron | 210/16 |
| 3,743,582 | 7/1973 | Kitai et al. | 435/310 |
| 4,035,292 | 7/1977 | Himsley | 210/189 |
| 4,057,401 | 11/1977 | Boblitz | 435/316 |
| 4,100,023 | 7/1978 | McDonald | 435/316 |

Primary Examiner—Peter A. Hruskoci
Attorney, Agent, or Firm—Benjamin P. Reese, II

[57] ABSTRACT

A compact vertical array of concentrically stacked and interfaced anaerobic digestion modules which comprise an anaerobic digestion sub-system. Each individual digestion module is an open-ended reaction vessel having an external flange on each end. Each pair of adjacent reaction vessels has a suitably sloped plate positioned at their interface and fastened to the bottom flange of the upper vessel and the top flange of the lower vessel. In this manner, each plate creates two individual digestion modules by serving as a bottom for the reaction vessel immediately above it and as a top for the reaction vessel immediately below it. Suitable openings are provided between adjacent digestion modules for transfer of digesting slurry from the module above to the module below. Each such opening is provided with a suitable valve for closing the opening during normal anaerobic digestion operations.

3 Claims, 3 Drawing Figures

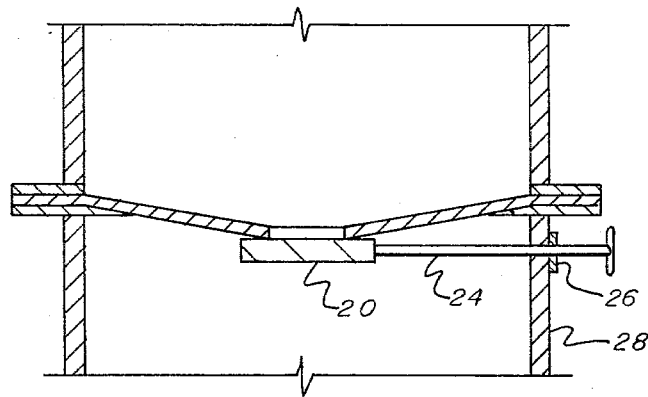
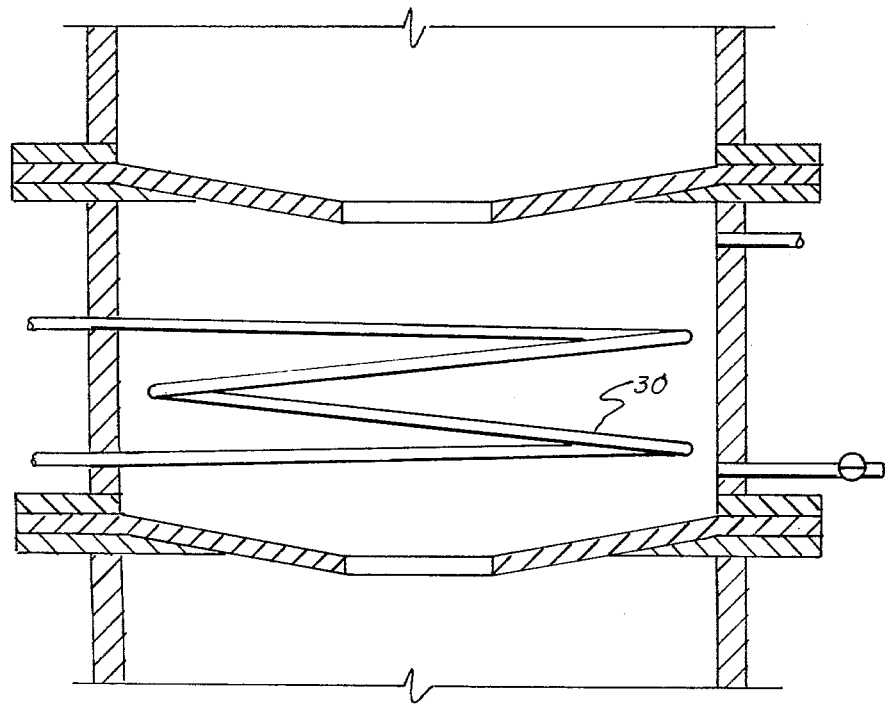

STACKED MODULES FOR ANAEROBIC DIGESTION

BACKGROUND OF THE INVENTION

This invention relates to new and improved anaerobic digestion modules useful as components of a system for production of methane gas by anaerobic digestion of feed materials containing suitable organic materials. In particular, this invention relates to vertically stacked anaerobic digestion modules which comprise an anaerobic digestion sub-system suitable for use with the system disclosed in the closely related U.S. Patent Application Ser. No. 56,545, filed by David J. Fischer, et al. on July 11, 1979, for a System and Process for Anaerobic Digestion, which is hereby incorporated by reference.

The system for production of methane gas by anaerobic digestion disclosed and claimed in Application Ser. No. 56,545 is comprised of a feed material pre-treatment sub-system, a slurry preparation sub-system, an anaerobic digestion sub-system, a gas collection sub-system, a gas storage sub-system, a sludge separation sub-system and a particle separation sub-system. The anaerobic digestion sub-system disclosed in that application is comprised of a plurality of individual digestion modules arranged to accommodate a multi-stage anaerobic digestion process. In the preferred embodiment disclosed in that application, each individual digestion module is a cylindrically shaped reaction vessel, such as a conventional fifty-five gallon drum, positioned on its side with its slurry inlet port at a slightly lower elevation than the slurry outlet port of the preceding digestion module. In addition, each individual digestion module is positioned on an incline with its slurry outlet port slightly lower than its slurry inlet port.

The structural arrangement of digestion modules disclosed in Application Ser. No. 56,545 allows gravity transfer of the digesting slurry from one digestion module to the next successive digestion module. It can be readily appreciated that such a structural arrangement of digestion modules does not require pumps for transferring the digesting slurry. Also, with such a structural arrangement, no mechanical mixers are necessary for mixing the digesting slurry in each digestion module. Sufficient mixing occurs when the digesting slurry is transferred from one digestion module to the next successive digestion module.

While an anaerobic digestion sub-system utilizing the structural arrangement of digestion modules disclosed in the Application Ser. No. 56,545 has these and other advantages, an extensive structural frame is required for its vertical support. And, it is desirable to include an operator walkway as a component of the structural frame. Since the number of individual digestion modules in the anaerobic digestion sub-system disclosed in that application varies depending upon the particular feed material to be digested, a standard design for the structural frame for those modules is not possible. Furthermore, a structural frame of the type which is required to support those modules does not lend itself to fabrication in a manufacturing plant prior to field installation of the modules. For these reasons, expensive custom design and field fabrication will be required for most installations of anaerobic digestion sub-systems using the structural arrangement of digestion modules disclosed in Application Ser. No. 56,545.

While an anaerobic digestion sub-system using the structural arrangement of digestion modules disclosed in Application Ser. No. 56,545 does not have to be installed inside a building, it is better practice to do so. First, it is difficult to maintain and control the temperature in the digestion modules if the sub-system is installed outside. Next, such a structural arrangement of digestion modules exposes a substantial surface area to the elements. Unless either expensive stainless steel construction or inside installation is used, frequent cleaning and maintenance of the modules and their structural frame will be required.

It will be readily appreciated that the structural arrangement of digestion modules disclosed in Application Ser. No. 56,545 requires extensive piping for interconnection of the individual modules. Not only are expensive piping materials required, but also expensive field welding operations are required to fabricate the anaerobic digestion sub-system. In many countries where anaerobic digestion systems would be desired, it is often difficult to employ qualified field construction welders.

It is desirable to have a plurality of anaerobic digestion modules which comprise an anaerobic digestion sub-system having all of the advantages of the structural arrangement of digestion modules disclosed in Application Ser. No. 56,545 without the foregoing and other disadvantages inherent in such a structural arrangement. Preferably, the operating characteristics of the resulting sub-system would be identical or superior to those of the sub-system disclosed in that application. It is also desirable to have a modular anaerobic digestion sub-system capable of being fabricated in a manufacturing plant and transported by barge, boat, rail or truck shipment to the site selected for installation of the anaerobic digestion system using the sub-system. And, of course, it is desirable for such a sub-system to be comprised of standard components which enable the system designer to easily vary the number of digestion modules in the sub-system without major perturbations in the normal operations of the manufacturing plant which fabricates such sub-systems.

SUMMARY OF THE INVENTION

This invention provides new and improved anaerobic digestion modules which overcome the disadvantages inherent in the structural arrangement of digestion modules disclosed in U.S. Patent Application Ser. No. 56,545, filed by David J. Fischer, et al. on July 11, 1979, for a System and Process for Anaerobic Digestion. The present invention overcomes those disadvantages without sacrificing the advantages of the structural arrangement of digestion modules disclosed in that application. With the present invention, standard components can be used to fabricate an anaerobic digestion sub-system having a plurality of digestion modules. Fabrication can be accomplished in a manufacturing plant and the completed sub-system can be transported by barge, boat, rail or truck to the site selected for the installation of the anaerobic digestion system using the sub-system.

The present invention provides a plurality of vertically stacked and directly interconnected anaerobic digestion modules. Each individual digestion module is an open-ended reaction vessel having an external flange on each end. The individual reaction vessels are concentrically stacked and interfaced in a compact vertical array with a suitably sloped plate positioned between adjacent reaction vessels. Thus, each plate functions as a bottom for the digestion module which is located immediately above it and a top for the digestion module which is located immediately below it.

Suitable openings are provided between adjacent digestion modules to function as a slurry outlet port for the upper digestion module and a slurry inlet port for the lower digestion module. During normal anaerobic digestion operations, a suitable valve closes each of these openings. When it is desired to transfer digesting slurry from one digestion module to the next successive digestion module, the valve closing the opening between the upper module containing the slurry to be transferred and the lower module to which transfer is desired is opened to allow the digesting slurry to flow from the upper module to the lower module. During such transfer operations, significant mixing of the digesting slurry takes place and solids which have settled during the retention period in the upper module are resuspended in the lower module. Various conventional valves, such as a slide valve or a ball valve, are suitable for this purpose.

A coiled tube for circulation of steam or hot water is positioned in the interior of each digestion module to provide means for heating the digesting slurry in the module. The steam or hot water enters the coiled tube from a high temperature steam or hot water input manifold and exits the coiled tube into a low temperature steam or water discharge manifold. Each coiled tube has a suitable valve for controlling the flow of steam or hot water through the tube and maintaining the desired temperature. With the structural arrangement of the present invention, heat losses from the individual digestion modules are minimized. Thus, the heat necessary to maintain the desired temperature in each module is substantially less than would be necessary with other structural arrangements of digestion modules. And, of course, with this structural arrangement of digestion modules, substantial savings in heat insulation costs are realized.

A gas sampling and discharge port having a three-way valve is provided near the top of each digestion module. Each of these ports is connected to a gas collection manifold. The system operator can use the three-way valve to either sample the gas production in the module or continuously transfer such gas to the gas collection manifold. If desired, a plurality of valves can be provided in the gas collection manifold to divert gases produced in individual modules or groups of modules to appropriate locations for storage or subsequent processing, or both, without mixing the gases produced in the individual modules or groups of modules.

A sample port having a two-way valve is provided near the bottom of each digestion module to enable the system operator to sample the digesting slurry in the module. The sample withdrawn from each such port can be analyzed to provide chemical, physical, microbiological and enzyme distribution data necessary for control of the anaerobic digestion processes in each individual module. In addition, the sample port can be used to add appropriate materials to adjust the pH of the digesting slurry in the module and to add microbes, enzymes, catalysts and other materials suitable for enhancing methane gas production.

A suitable top cover is provided for the top digestion module in the vertical array. The top cover has a slurry inlet port to transfer freshly prepared slurry from a suitable slurry preparation sub-system to the top or initial digestion module. A suitable bottom cover is provided for the bottom or final digestion module in the vertical array. The bottom cover has a slurry outlet port to transfer digested slurry to a suitable sludge separation sub-system. The vertical array of digestion modules is supported by a plurality of support posts.

These and many other advantages, features and objects of the present invention will be apparent from the following brief description of drawings, description of the preferred embodiment and claims.

BRIEF DESCRIPTION OF DRAWINGS

FIG. 2 is a sectional view through lines 2—2 in FIG. 1. This view illustrates details of a sliding valve which is suitable for closing the opening through the plate used between each adjacent digestion module.

FIG. 3 is an elevational view, in section, of a typical digestion module illustrating a coiled tube positioned in the interior of the module.

DESCRIPTION OF THE PREFERRED EMBODIMENT

Figure 1:
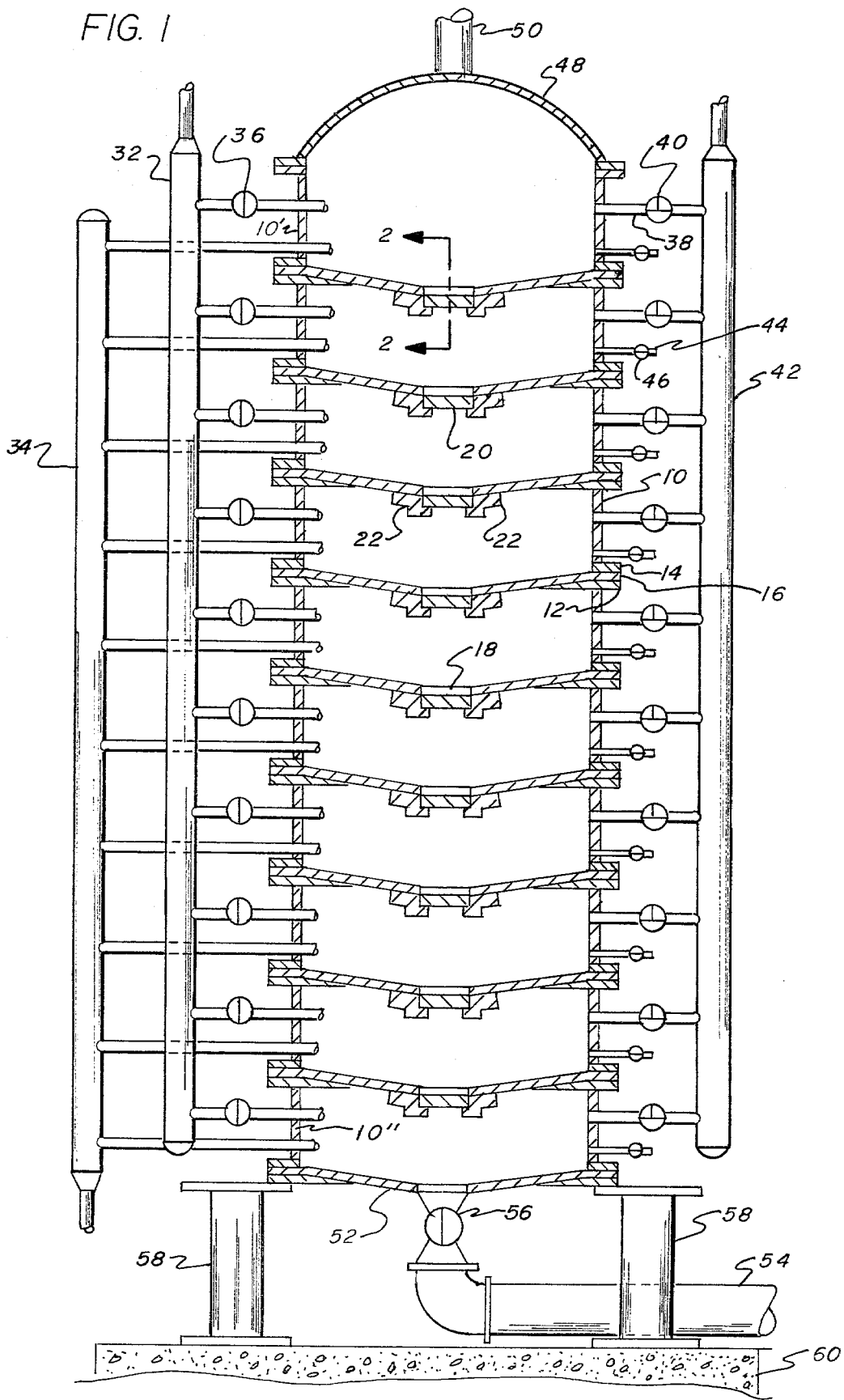
FIG. 1 is an elevational view, in section, of the vertically stacked anaerobic digestion modules of the present invention.

The vertically stacked anaerobic digestion modules of the present invention are illustrated in FIGS. 1, 2 and 3. Ten digestion modules are illustrated in FIG. 1, but the total number of digestion modules actually used for each individual anaerobic digestion sub-system will vary depending upon both the nature of the feed materials to be digested in the sub-system and the operating temperature of each individual module in the sub-system.

Referring to FIG. 1, a plurality of digestion modules 10 are concentrically stacked and interfaced in a compact vertical array. Each module 10 is an open-ended cylindrically shaped reaction vessel having an upper flange 12 and a lower flange 14. A conical-shaped plate 16 is positioned between adjacent digestion modules 10. With this arrangement, each plate 16 functions as a bottom for the digestion module 10 immediately above the plate and as a top for the digestion module 10 immediately below the plate. Conventional fastening means, such as bolts and nuts, are used to fasten the opposed flanges 12 and 14 of adjacent digestion modules 10 and the plate 16 is positioned there between.

Each conical-shaped plate 16 has an opening 18 through its center. The opening 18 functions as a slurry outlet port for the digestion module 10 immediately above the plate 16 and a slurry inlet port for the digestion module 10 immediately below the plate 16. A conventional slide valve 20 is provided to close each opening 18 during normal anaerobic digestion operations. The slide valve 20 is operatively positioned below the opening 18 with a pair of support brackets 22.

Referring to FIG. 2, the valve 20 has an operating rod 24 connected thereto which passes through a conventional seal 26 positioned in a cylindrical opening through the wall 28 of the digestion module 10. It will be readily appreciated that this provides means for opening and closing the valve 20 from the exterior of the digestion module 10. The valve 20 is maintained in an open mode when transferring digesting slurry from an upper digestion module 10 to the digestion module 10 immediately below. Accordingly, all transfers of digesting slurry are efficiently accomplished by gravity flow. And, the digesting slurry is mixed by the transfer thereby resuspending solids which settled in the upper module.

While the digestion modules 10 which have been described and illustrated have circular cross sections, other geometric shapes are suitable for the modules 10. And, of course, the plates 16 need not be conical shaped. With respect to these features, the present invention requires only that each plate 16 have a downward slope which is sufficient in magnitude for efficient flow of digesting slurry during transfers of slurry from a digestion module 10 to the module 10 immediately below. For example, each plate 16 could be in the shape of a distorted cone having its low point located away from the center of the digestion module 10. Or, each plate 16 could be a flat plate positioned on an incline to the horizontal.

With many of these alternate embodiments, the opening 18 in the plates 16 can be located nearer the outer walls of the digestion modules 10. In such cases, the operating rods 24 could be substantially shortened. And, of course, if the plates 16 are flat plates inclined to the horizontal, it may be desirable to locate the openings 18 through the side walls of the digestion modules 10 so that the valves 20 can be located outside of the digestion modules 10. This would, of course, greatly simplify valve maintenance procedures. It will be readily appreciated that many types of conventional valves, such as ball valves, can be substituted for the slide valves 20 which have been described and illustrated.

To heat the digesting slurry in each digestion module 10, a coiled tube 30 is positioned in the interior of the module. Either steam or hot water can be circulated through each coiled tube 30 in appropriate quantities to provide the necessary heat and to maintain the desired temperature. The steam or hot water enters the coiled tube 30 from a high temperature steam or water input manifold 32 and exits the coiled tube 30 into a low temperature steam or water discharge manifold 34. A suitable valve 36 is provided in the input side of the coiled tube 30 to control the flow of steam or hot water through the tube. It will be readily appreciated that other conventional heating means could be substituted for the coiled tubes 30. Suitable insulation materials are installed around the exterior surfaces of each digestion module 10.

Each digestion module 10 has a gas sampling and discharge port 38 near its top. A three-way valve 40 is provided in each gas sampling and discharge port 38. And, each gas sampling and discharge port 38 is connected to a gas collection manifold 42. If the three-way valve 40 is positioned in the appropriate mode, the system operator can sample the gas production in the digestion module 10. During normal anaerobic digestion operations, the three-way valve 40 will be positioned in an appropriate mode for continuous transfer of the gas produced in the module 10 to the gas collection manifold 42.

A plurality of conventional valves can be provided in the gas collection manifold 42 to divert the gases produced in the individual digestion modules 10, or groups of modules, for storage or subsequent processing, or both, without mixing the gases produced in the individual digestion modules 10, or groups of modules. With this arrangement, less separative work is required for separation of gases produced in the modules into methane and carbon dioxide components A sample port 44 having a two-way valve 46 is positioned near the bottom of each digestion module 10. These sample ports 44 provide means for withdrawal of samples of digesting slurry by the system operator for subsequent chemical, physical, microbiological and enzyme distribution analysis. Such analyses are necessary to obtain data used to control the anaerobic digestion processes in each digestion module 10. Furthermore, if desired, the system operator can use the sample port 44 either to add appropriate materials to adjust the pH of the digesting slurry in the digestion module 10 or to add microbes, enzymes, catalysts and other materials suitable for enhancing methane gas production.

A top cover 48 is provided for the top digestion module 10' in the vertical array. Conventional means, such as bolts and nuts, are used for fastening the top cover 48 to the top flange 12 of the top module 10'. The top cover 48 has a slurry inlet port 50 for transfer of freshly prepared slurry from a suitable slurry preparation subsystem to the top digestion module 10'.

A bottom cover 52 is provided for the bottom digestion module 10" in the vertical array. Conventional means, such as bolts and nuts, are used for fastening the bottom cover 52 to the bottom flange 14 of the bottom module 10". The bottom cover 52 has a slurry outlet port 54 for transfer of digested slurry from the bottom digestion module 10" to a suitable sludge separation sub-system. If a suitable valve is not included in the inlet port of the sludge separation sub-system, valve 56 is provided in the slurry outlet port 54. Conventional means, such as bolts and nuts, are used to attach the bottom cover 52 to the top of a plurality of support posts 58 resting on a suitable support footing 60. While not absolutely required, the support posts 58 can be fastened to the support footing 60 by conventional means, such as screws, if desired. In this manner, the vertical array of digestion modules 10 is supported by a single, inexpensive support stand. While a plurality of support posts have been illustrated, it will be readily appreciated that many other inexpensive support structures are suitable for this purpose.

The vertical array of anaerobic digestion modules 10 which has been described is suitable for use as an anaerobic digestion sub-system of the type disclosed in U.S. Patent Application Ser. No. 56,545, filed by David J. Fischer, et al. on July 11, 1979, for a System and Process for Anaerobic Digestion. Operation of such a sub-system as a component of an anaerobic digestion system is fully described in that application While the present invention has been disclosed in connection with the preferred embodiment thereof, it should be understood that there may be other embodiments which fall within the spirit and scope of the invention as defined by the following claims.

We claim:

1. An anaerobic digestion sub-system for a system for production of methane gas by anaerobic digestion of feed materials containing suitable organic materials, comprising:

(a) a plurality of anaerobic digestion modules, stacked and interfaced in a vertical array, each having a gas sampling and discharge port having a three-way valve positioned therein and each having a digesting slurry sample port having a valve positioned therein;

(b) a plurality of sloped plates, each positioned between a pair of adjacent digestion modules to function as a bottom for the digestion module immediately above it and as a top for the digestion module immediately below it and each having an opening through its lowest point for transfer of digesting slurry from the digestion module immediately above it to the digestion module immediately below it;

(c) a plurality of valves, each operatively positioned for closing one of said openings through said plates during anaerobic digestion operations;

(d) means for independently operating each of said valves from the exterior of said anaerobic digestion modules;

(e) a top cover fastened to the top digestion module in said vertical array, said top cover having a slurry inlet port for transfer of freshly prepared slurry from a slurry preparation sub-system to said top digestion module;

(f) a bottom cover fastened to the bottom digestion module in said vertical array, said bottom cover having a slurry outlet port for transfer of digested slurry from said bottom digestion module to a sludge separation sub-system;

(g) a valve positioned in said slurry outlet port of said bottom digestion module for closing said slurry outlet port during anaerobic digestion operations;

(h) means for independently heating and controlling the temperature in the interior of each of said anaerobic digestion modules; and (i) a gas collection manifold for collecting gas from the gas sampling and discharge ports.

2. An anaerobic digestion sub-system as recited in claim 1, wherein said valves operatively positioned for closing said openings through said plates are slide valves.

3. An anaerobic digestion sub-system as recited in claim 1, wherein said means for heating and controlling the temperature in the interior of each of said digestion modules comprises: a plurality of coiled tubes, each positioned in the interior of one digestion module; an input manifold connected to said coiled tubes for admission of steam or hot water to said coiled tubes; a discharge manifold connected to said coiled tubes for exit of steam or hot water from said coiled tubes; and a plurality of valves, each for independent control of the flow of steam or hot water through one coiled tube.

* * * * *